(12) United States Patent
DeLegge et al.

(10) Patent No.: US 8,382,770 B2
(45) Date of Patent: Feb. 26, 2013

(54) METHOD FOR IMPLANTING A PERCUTANEOUS ENDOSCOPIC GASTROSTOMY/JEJUNOSTOMY TUBE IN A PATIENT AND ACCESS NEEDLE FOR USE IN SAID METHOD

(75) Inventors: Rebecca DeLegge, Mt. Pleasant, SC (US); Mark DeLegge, Mt. Pleasant, SC (US); Laurence D. Brenner, Boylston, MA (US); Mark L. Adams, Sandy, UT (US); Michele Carter, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/301,432

(22) Filed: Nov. 21, 2011

(65) Prior Publication Data

US 2012/0095405 A1    Apr. 19, 2012

Related U.S. Application Data

(62) Division of application No. 10/300,702, filed on Nov. 20, 2002, now abandoned.

(60) Provisional application No. 60/335,681, filed on Nov. 21, 2001, provisional application No. 60/418,990, filed on Oct. 15, 2002.

(51) Int. Cl.
*A61F 11/00* (2006.01)
(52) U.S. Cl. ........................................ 606/108
(58) Field of Classification Search ......... 606/1, 108, 606/142, 185; 604/157, 158, 164.01, 164.04, 604/176, 500, 506, 523; 600/435; 128/898
See application file for complete search history.

(56) References Cited

U.S. PATENT DOCUMENTS

| 1,248,492 A | 12/1917 | Hill |
| 3,225,762 A | 12/1965 | Guttman |
| 3,993,079 A | 11/1976 | Henriques de Gatztanondo |
| 4,230,123 A | 10/1980 | Hawkins, Jr. |
| 4,269,186 A | 5/1981 | Loveless et al. |
| 4,826,481 A | 5/1989 | Sacks et al. |
| 4,861,334 A | 8/1989 | Nawaz |
| 4,900,306 A | 2/1990 | Quinn et al. |
| 5,078,743 A | 1/1992 | Mikalov et al. |

(Continued)

FOREIGN PATENT DOCUMENTS

| DE | 4038952 A1 | 6/1992 |
| EP | 0583049 A1 | 2/1994 |

(Continued)

OTHER PUBLICATIONS

International Search Report for PCT Application No. PCT/EP02/13022, mailed Mar. 13, 2003.

*Primary Examiner* — Gary Jackson
*Assistant Examiner* — Eric Blatt
(74) *Attorney, Agent, or Firm* — Kenyon & Kenyon LLP

(57) ABSTRACT

Method for implanting a percutaneous endoscopic jejunostomy tube in a patient and access needle for use in the method. In one embodiment, the method comprises the steps of (a) providing an access needle wherein the distal end of the stylet extends distally for an appreciable distance beyond the distal end of the cannula; (b) inserting the stylet, but not the cannula, into the jejunum; (c) grabbing the stylet with an endoscopically-positioned snare; (d) anchoring the jejunum against the abdominal wall using the snared stylet; (e) loosening the snare slightly while advancing the cannula into the jejunum and into the loosened snare; (f) tightening the snare around the cannula; (g) removing the stylet from the cannula; (h) inserting a guide wire or suture through the cannula into the jejunum; and (i) proceeding in the conventional fashion to implant a PEJ tube into the patient using the guide wire or suture.

17 Claims, 9 Drawing Sheets

U.S. PATENT DOCUMENTS

| | | |
|---|---|---|
| 5,112,310 A | 5/1992 | Grobe |
| 5,167,627 A | 12/1992 | Clegg et al. |
| 5,306,259 A | 4/1994 | Fischell et al. |
| 5,318,543 A | 6/1994 | Ross et al. |
| 5,391,159 A | 2/1995 | Hirsch et al. |
| 5,531,678 A | 7/1996 | Tomba et al. |
| 5,672,158 A | 9/1997 | Okada et al. |
| 5,851,195 A | 12/1998 | Gill |
| 5,984,941 A | 11/1999 | Wilson et al. |
| 6,030,364 A | 2/2000 | Durgin et al. |
| 6,090,073 A | 7/2000 | Gill |
| 6,319,266 B1 | 11/2001 | Stellon et al. |
| 6,673,058 B2 | 1/2004 | Snow |
| 6,689,142 B1 | 2/2004 | Tremaglio, Jr. et al. |
| 6,808,519 B2 | 10/2004 | Fanelli et al. |
| 6,910,581 B2 | 6/2005 | McMichael et al. |

FOREIGN PATENT DOCUMENTS

| | | |
|---|---|---|
| WO | 94/27524 A1 | 12/1994 |

METHOD FOR IMPLANTING A PERCUTANEOUS ENDOSCOPIC GASTROSTOMY/JEJUNOSTOMY TUBE IN A PATIENT AND ACCESS NEEDLE FOR USE IN SAID METHOD

CROSS-REFERENCE TO RELATED APPLICATIONS

The present application is a divisional of U.S. application Ser. No. 10/300,702, filed Nov. 20, 2002, now abandoned which claims the benefit under 35 U.S.C. 119(e) of U.S. Provisional Patent Application Serial No. 60/335,681, filed Nov. 21, 2001, and of U.S. Provisional Patent Application Ser. No. 60/418,990, filed Oct. 15, 2002, all of which are incorporated herein by reference.

BACKGROUND OF THE INVENTION

The present invention relates generally to percutaneous endoscopic gastrostomy (PEG) tubes and percutaneous endoscopic jejunostomy (PEJ) tubes and methods for their implantation in a patient and relates more particularly to a novel method for implanting a PEG tube or a PEJ tube in a patient and to a novel access needle for use in said method.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy and result in the implantation of a gastrostomy feeding tube assembly (also referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to "the push method," the distal end of an endoscope is inserted into a patient's mouth and is passed through the esophagus into the stomach. After distension of the stomach by inflation with air, an entry site on the abdomen is identified, and an incision is made by passing a needle (or stylet) with an outer cannula through the abdominal wall and into the stomach. The needle is then removed while keeping the cannula in place. Next, a snare is inserted into the stomach via the endoscope and is looped over the distal end of the cannula. A first end of a flexible guide wire is then passed through the cannula and into the stomach where it is grasped by the snare, the second end of the guide wire remaining external to the patient. The endoscope and the snare are then withdrawn from the mouth of the patient to deliver the first end of the guide wire.

A catheter assembly is then inserted over the first end of the guide wire and is pushed over the guide wire towards its second end. The catheter assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the catheter assembly over the guide wire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the gastric wall.

With the internal bolster in place against the gastric wall, a proximal portion of the implanted gastrostomy feeding tube is then typically cut and removed from the implanted tube to reduce the externally-extending portion of the tube to a desired length. An external bolster is typically secured to the remaining implanted portion of the feeding tube to engage the abdomen in such a way as to prevent longitudinal movement of the feeding tube within the stoma tract. Additionally, a "Y-port" adapter is typically attached to the proximal end of the implanted feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

"The pull method" differs from "the push method" in that, after removal of the entry needle from the cannula, a first end of a suture is passed through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a catheter assembly comprising a gastrostomy feeding tube having an internal bolster at its trailing end and a plastic fitting at its leading end. The plastic fitting has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the catheter assembly is then pulled retrograde through the patient until the gastrostomy feeding tube emerges from the abdomen of the patient and the internal bolster engages the gastric wall of the patient. Next, as is the case in "the push method," the implanted gastrostomy feeding tube is typically cut to a desired length, an external bolster is typically secured to the cut implanted tube, a Y-port adapter is typically attached to the proximal end of the implanted feeding tube, and a detachable locking clip is typically secured to the implanted feeding tube at a point between the external bolster and the Y-port adapter.

Although gastrostomies are the most common approach to the long-term feeding of patients unable to swallow, there are situations in which it is desirable to provide food directly into a patient's jejunum without passing through the patient's stomach. This has typically been accomplished by using a technique similar to that described above to implant a feeding tube into the jejunum, instead of into the stomach. One difficulty, however, that has been encountered in implanting feeding tubes into the jejunum has been in the piercing of the jejunum by the needle/cannula assembly (said assembly also referred to in the art as "an access needle") so as to create an insertion hole through which a guide wire or suture may be inserted. This difficulty arises, in part, because the jejunum is narrow and thus hard to locate externally and, in part, because the jejunum is not fixed within the body at any particular location. As a result, not only is it difficult to actually pierce the jejunum with an access needle (the access needle frequently missing the jejunum or just pushing the jejunum aside without penetrating it), but even if the jejunum is actually pierced by the access needle, subsequent movement of the jejunum may cause the access needle to become dislodged therefrom. Consequently, it is generally desirable to use as small a diameter needle as possible to pierce the jejunum. This maximizes the chance that the jejunum, if struck by the access needle, will be pierced thereby and also minimizes the size of the insertion hole (which is desirable for obvious reasons).

One approach that has recently been devised to address the above-identified problems with piercing the jejunum involves piercing the jejunum with a small diameter needle, grabbing the distal end of the needle with an endoscopically-placed snare, using said small diameter needle (with the snare secured thereto) to anchor the jejunum against the abdominal wall, piercing the thus-anchored jejunum with an access needle at a site proximate to the first piercing site, transferring the snare from the small diameter needle to the cannula of the access needle, removing the small diameter needle from the jejunum, and then proceeding in the conventional fashion by removing the needle of the access needle from its cannula, inserting a guide wire or suture into the cannula for grabbing by the snare, etc.

Access needles of the type that are typically used in percutaneous endoscopic gastrostomies and in percutaneous endoscopic jejunostomies have their genesis in radiology and cardiology and typically come in two different varieties. One such access needle is referred to in the art as a Seldinger needle and comprises a solid metal needle (or stylet) removably mounted within a metal cannula. A plastic needle hub is fixed to the proximal end of the metal needle, and a plastic cannula hub is fixed to the proximal end of the metal cannula. The needle hub and the cannula hub are sized and shaped to permit a portion of the needle hub to be removably inserted into the cannula hub in such a way as to delimit insertion of the needle through the cannula. A tab is provided on the needle hub and a corresponding slot is provided on the cannula hub, said slot being adapted to receive said tab in order to permit said needle and said cannula to be placed in a particular rotational orientation relative to one another. The cannula hub is also shaped to include a lateral flange upon which a user may rest, for example, his forefinger and middle finger.

The other type of access needle commonly used to perform percutaneous endoscopic gastrostomies and jejunostomies is referred to in the art as an Angiocath needle and comprises a hollow metal needle removably mounted within a plastic cannula. A plastic needle hub is fixed to the proximal end of the metal needle, and a plastic cannula hub is fixed to the proximal end of the plastic cannula. The needle hub and the cannula hub are sized and shaped to permit a portion of the needle hub to be removably inserted into the cannula hub in such a way as to delimit insertion of the needle through the cannula. No means is provided in an Angiocath needle for fixing the rotational orientation of the needle relative to the cannula when the needle hub is inserted into the cannula hub.

In both a Seldinger needle and an Angiocath needle, the lengths of the needle and the cannula are such that, with the needle fully inserted into the cannula, only the needle tip extends distally beyond the distal end of the cannula. Seldinger needles typically have a smaller diameter than do Angiocath needles (20 gauge needle and 18 gauge cannula vs. 16 gauge needle and 14 gauge cannula, respectively); however, more doctors have been trained using Angiocath needles and, therefore, are more comfortable with and use Angiocath needles.

In both a Seldinger needle and an Angiocath needle, it is possible for the needle to be withdrawn unintentionally from its respective cannula as no means is provided in either device for longitudinally securing the needle hub to its respective cannula hub.

SUMMARY OF THE INVENTION

It is an object of the present invention to provide a novel method for implanting in a patient a feeding tube, such as a PEG tube, a PEJ tube or the like.

It is another object of the present invention to provide a method as described above which, as applied to PEJ tube implantation, overcomes at least some of the difficulties described above in connection with conventional PEJ implantation methods.

It is yet another object of the present invention to provide a novel access needle adapted for use in the above-described method.

Therefore, according to one aspect of the invention, there is provided an access needle, said access needle comprising, in a preferred embodiment, a stylet and a cannula, the stylet being slidably mounted within the cannula. A stylet hub is secured to the proximal end of the stylet, and a cannula hub is secured to the proximal end of the cannula. The stylet hub and the cannula hub are correspondingly threaded to permit the stylet and the cannula to be removably secured to one another. The stylet and the cannula are dimensioned relative to one another so that, when the stylet and the cannula are secured to one another, the stylet extends distally beyond the distal end of the cannula for a considerable distance. The distal end of the cannula is marked (e.g., by chemical etching) so as to be easily identifiable when viewed endoscopically. The respective diameters of the stylet and the cannula of the subject access needle are small, e.g., 20 gauge and 18 gauge, respectively.

According to another aspect of the invention, there is provided a method for implanting a PEJ tube in a patient, said method comprising, in a preferred embodiment, the steps of (a) providing an access needle wherein the distal end of the stylet extends distally for an appreciable distance beyond the distal end of the cannula; (b) inserting the distal end of the stylet, but not the distal end of the cannula, into the jejunum; (c) grabbing the distal end of the stylet with an endoscopically-positioned snare; (d) anchoring the jejunum against the abdominal wall of the patient using the snared stylet; (e) loosening the snare slightly while advancing the distal end of the cannula into the jejunum and into the loosened snare; (f)

tightening the snare around the distal end of the cannula; (g) removing the stylet from the cannula; (h) inserting a guide wire or suture through the cannula and into the jejunum; and (i) proceeding in the conventional fashion to implant a PEJ tube into the patient using said guide wire or suture.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
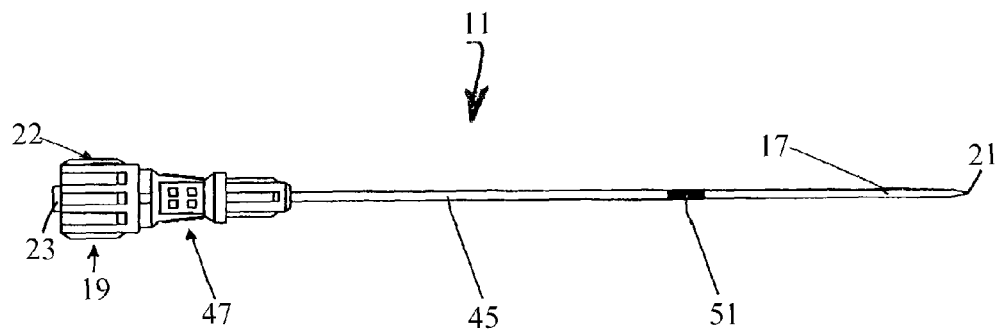
FIG. 1 is a side view of one embodiment of an access needle constructed according to the teachings of the present embodiment.
Figure 2:
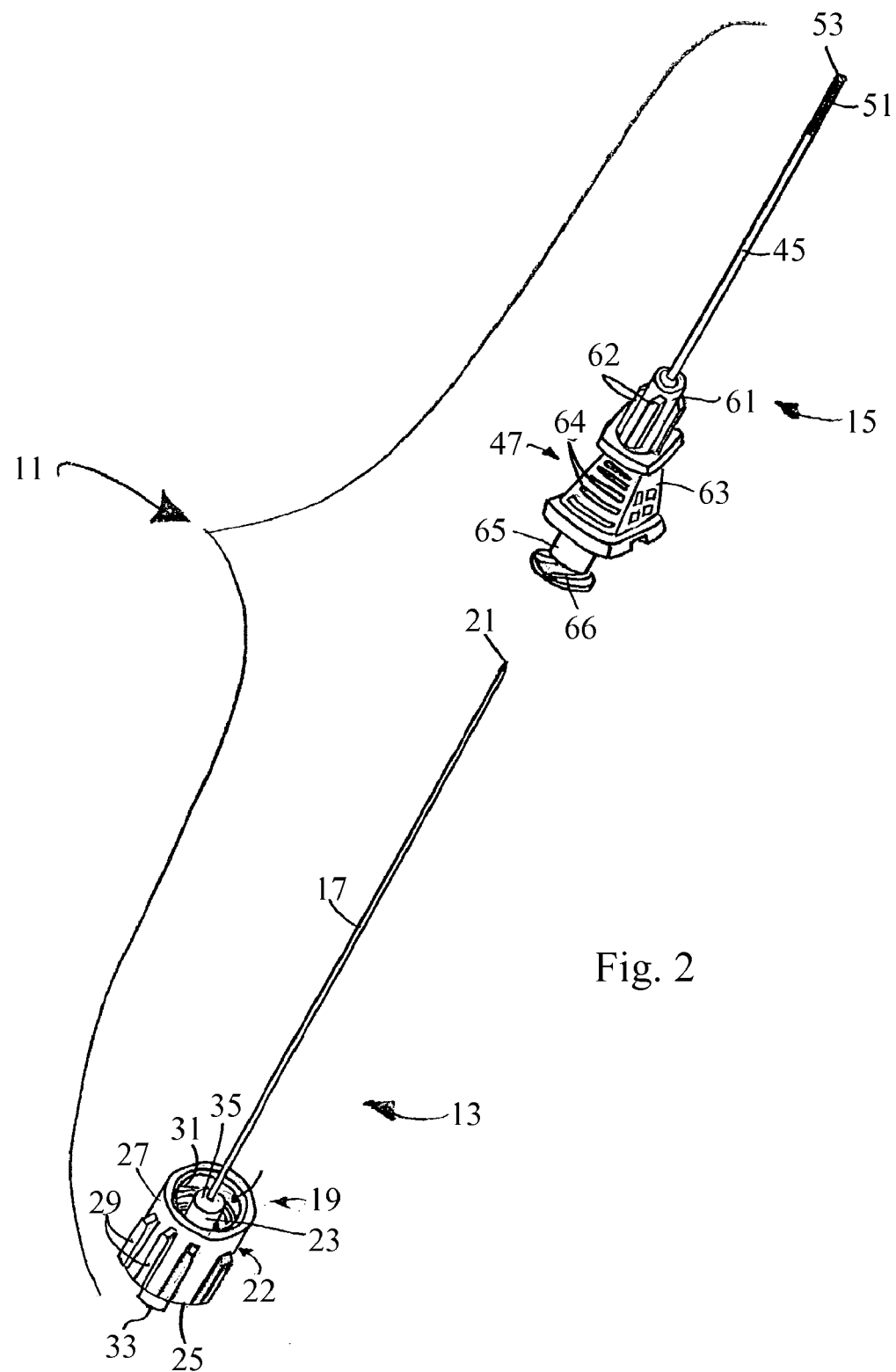
FIG. 2 is a partially exploded, perspective view of the access needle of FIG. 1.

Referring now to FIGS. 1 and 2, there are shown side and partially exploded perspective views, respectively, of a preferred embodiment of an access needle constructed according to the teachings of the present invention, said access needle being represented generally by reference numeral 11.

Access needle 11 comprises a stylet assembly 13 and a cannula assembly 15.

Figure 3:
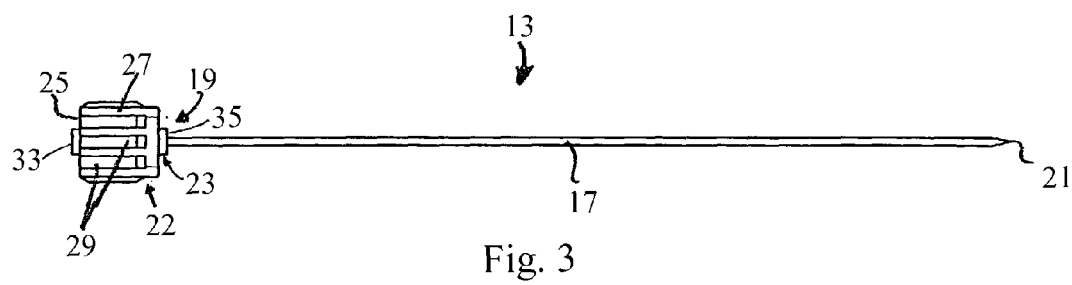
FIG. 3 is a side view of the stylet assembly shown in FIG. 1.
Figure 4:
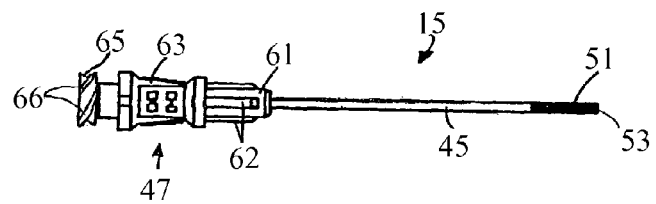
FIG. 4 is a side view of the cannula assembly shown in FIG. 1.
Figure 5:
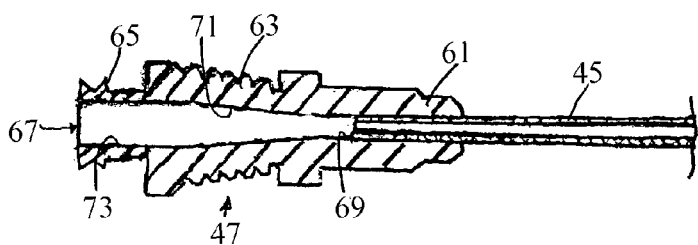
FIG. 5 is a fragmentary longitudinal section view of the cannula assembly shown in FIG. 1.

Referring now to FIGS. 1 through 3, stylet assembly 13 comprises a stylet (or sounding needle) 17 and a stylet hub 19. Stylet 17, which is preferably made of stainless steel, is a solid cylindrical member of small diameter, preferably 20 gauge, having a sharp, three-sided tip 21 at its distal end.

Hub 19 comprises a body 22 and a plug 23. Body 22, which is preferably made of plastic, is a generally cylindrical hollow member having a proximal end wall 25, a circular side wall 27 and an open distal end. The outer surface of side wall 27 is provided with a plurality of longitudinally extending ribs 29 to facilitate the gripping of body 22. The inner surface of side wall 27 is provided with a helical thread 31, the purpose of which will be described below. Plug 23, which is preferably made of plastic, is a generally cylindrical solid member fixedly mounted near its proximal end 33 within an opening (not shown) provided in end wall 25, plug 23 extending coaxially with side wall 27 to define therebetween an annular space 28. Stylet 17, which extends coaxially with plug 23, is fixed in distal end 35 of plug 23, preferably by insert-molding.

Referring now to FIGS. 1, 2, 4 and 5, cannula assembly 15 comprises a cannula 45 and a cannula hub 47. Cannula 45, which is preferably made of stainless steel, is a tubular member of small diameter, preferably 18 gauge, that is appropriately dimensioned for stylet 17 to be removably inserted thereinto. A circumferential band 51, which may be produced, for example, by chemical-etching or the like, extends proximally a short distance (e.g., approximately 3/10 inch or more) from the distal end 53 of cannula 45. Band 51, which is readily distinguishable in appearance, e.g., by color, from stylet 17, permits facile differentiation of stylet 17 and cannula 45, which is desirable for reasons to become apparent below.

Cannula hub 47, which is preferably made of plastic, is a unitary member shaped to include a distal portion 61, an intermediate portion 63, and a proximate portion 65. A plurality of longitudinal ribs 62 are formed on the outer surface of distal portion 61 to engage a protective sleeve (not shown) removably mounted over cannula 45 and stylet 17 when needle 11 is not in use. A plurality of laterally extending gripping elements 64 are formed on the outer surface of intermediate portion 63 to facilitate the gripping of hub 47 by a user. Proximate portion 65 is appropriately dimensioned to be received in annular space 28 of stylet hub 19. Threads 66 are formed on the outside surface of proximate portion 65 and are adapted to engage thread 31, thereby permitting hub 19 and hub 47 to be screwed (or twist-locked) together so as to prevent undesired relative longitudinal movement between stylet 17 and cannula 45.

A longitudinal bore 67 is formed in hub 47, bore 67 having a distal region 69 disposed in distal portion 61, an intermediate region 71 disposed in intermediate portion 63 and a proximal region 73 disposed in proximate portion 65. Distal region 69 is appropriately dimensioned to securely receive therewithin the proximal end of cannula 45. Proximal region 73 has a comparatively large diameter to facilitate the insertion of stylet 17 thereinto, and intermediate region 71 tapers in diameter from proximal region 73 to distal region 69 so as to facilitate the insertion of stylet 17 into cannula 45.

Stylet 17 and cannula 45 are dimensioned so that, when hub 19 and hub 47 are coupled together in the twist-lock manner described above, stylet 17 extends distally beyond distal end 53 of cannula 45 for a sufficient distance so that, as will hereinafter be described, tip 21 of stylet 17 may be inserted into a jejunum, without also inserting cannula 45 thereinto, and a snare may be tightened around the thus inserted portion of stylet 17. In the present embodiment, stylet 17 extends approximately 1.5 inch beyond distal end 53 of cannula 45, cannula 45 having a length of about 2.5 inches. (It should be understood, however, that the above dimensions of stylet 17 and cannula 45 may be varied. For example, stylet 17 and cannula 45 could be dimensioned so that cannula 45 has a length that is about ⅔ the length of stylet 17.)

Figure 6:
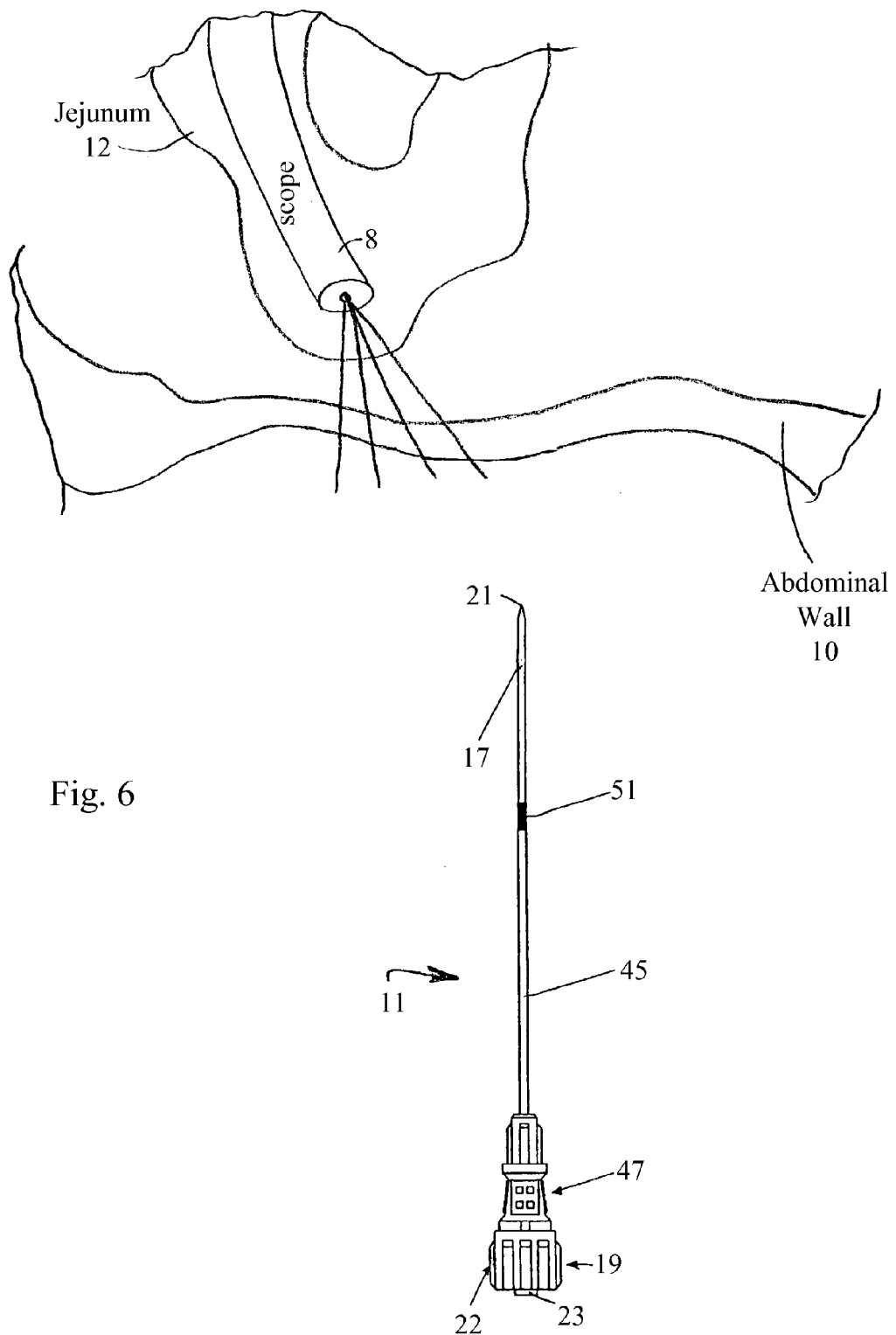
FIG. 6 is a schematic view showing the access needle of FIG. 1 just prior to its insertion into a patient during transillumination of the patient's jejunum.

The use of access needle 11 in the implantation of a PEJ tube in a patient in accordance with the teachings of the present invention will now be described. Referring now to FIG. 6, after properly administering an anesthetic to a patient, an endoscope 8 having an illuminating channel is inserted through the patient's mouth and into the digestive tract of the patient until it reaches the patient's jejunum. Scope 8 is used to transilluminate the jejunum through the abdominal wall, thereby identifying the location of the jejunum to a surgeon in order to facilitate the surgeon's insertion of access needle 11 through the abdominal wall 10 and into the jejunum 12 of the patient.

Figure 7:
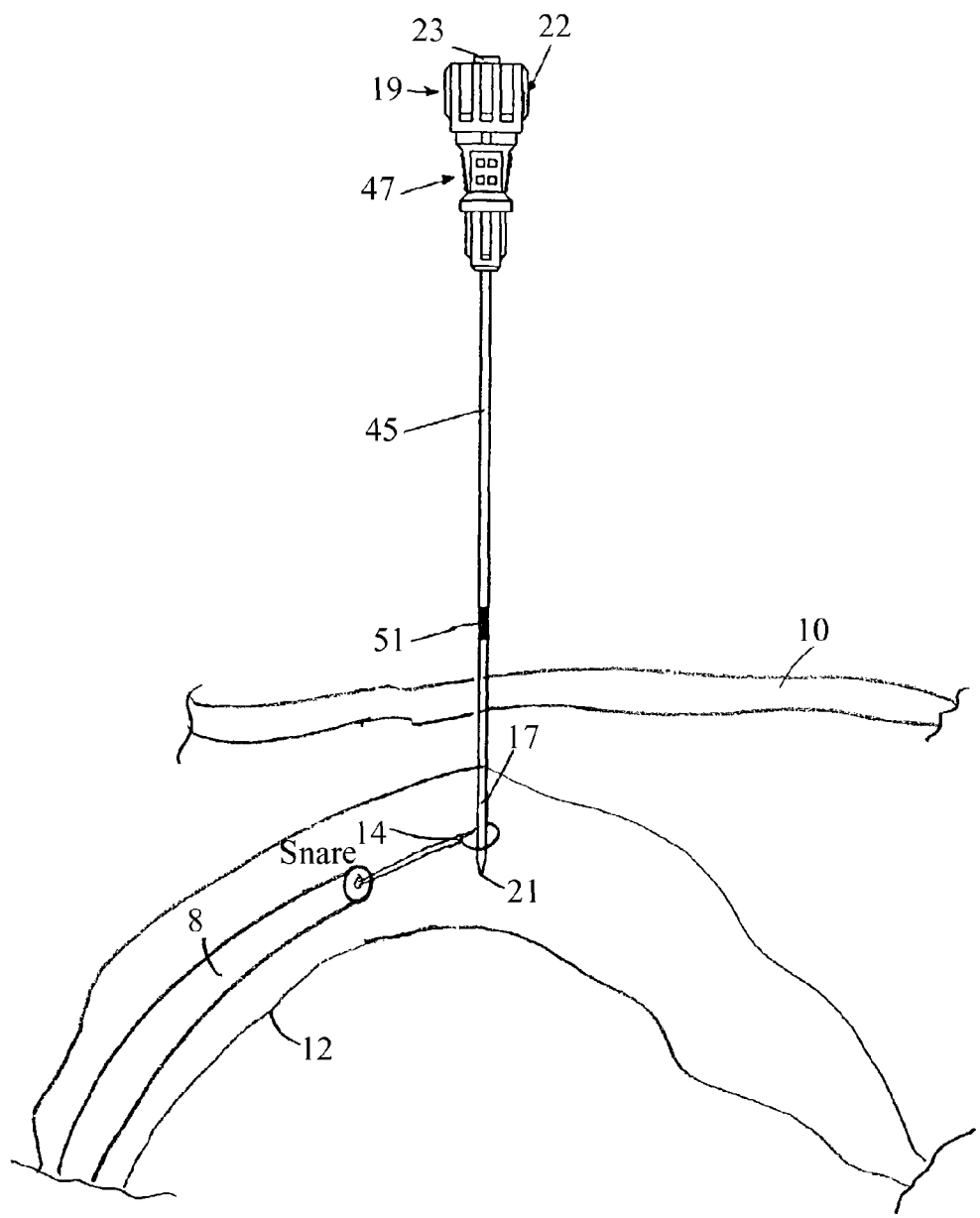
FIG. 7 is a schematic view showing the access needle of FIG. 1 inserted into the patient so that the distal end of the stylet of the access needle, but not the distal end of the cannula of the access needle, is inserted into the jejunum for capture by an endoscopic snare.

Referring now to FIG. 7, the distal end of stylet 17, but not cannula 45, is then inserted through abdominal wall 10 and into jejunum 12 until it is visible to endoscope 8 through an observation channel therein. A snare 14, which is inserted into the jejunum 12 through a snare channel of endoscope 8, is then used to securely capture the inserted end of stylet 17 and to couple stylet 17 to snare 14. With stylet 17 and snare 14 thus coupled, stylet 17 is pulled proximally so as to engage the wall of jejunum 12. Further pulling of stylet 17 results in jejunum 12 being held stationary against abdominal wall 10.

Figure 8:
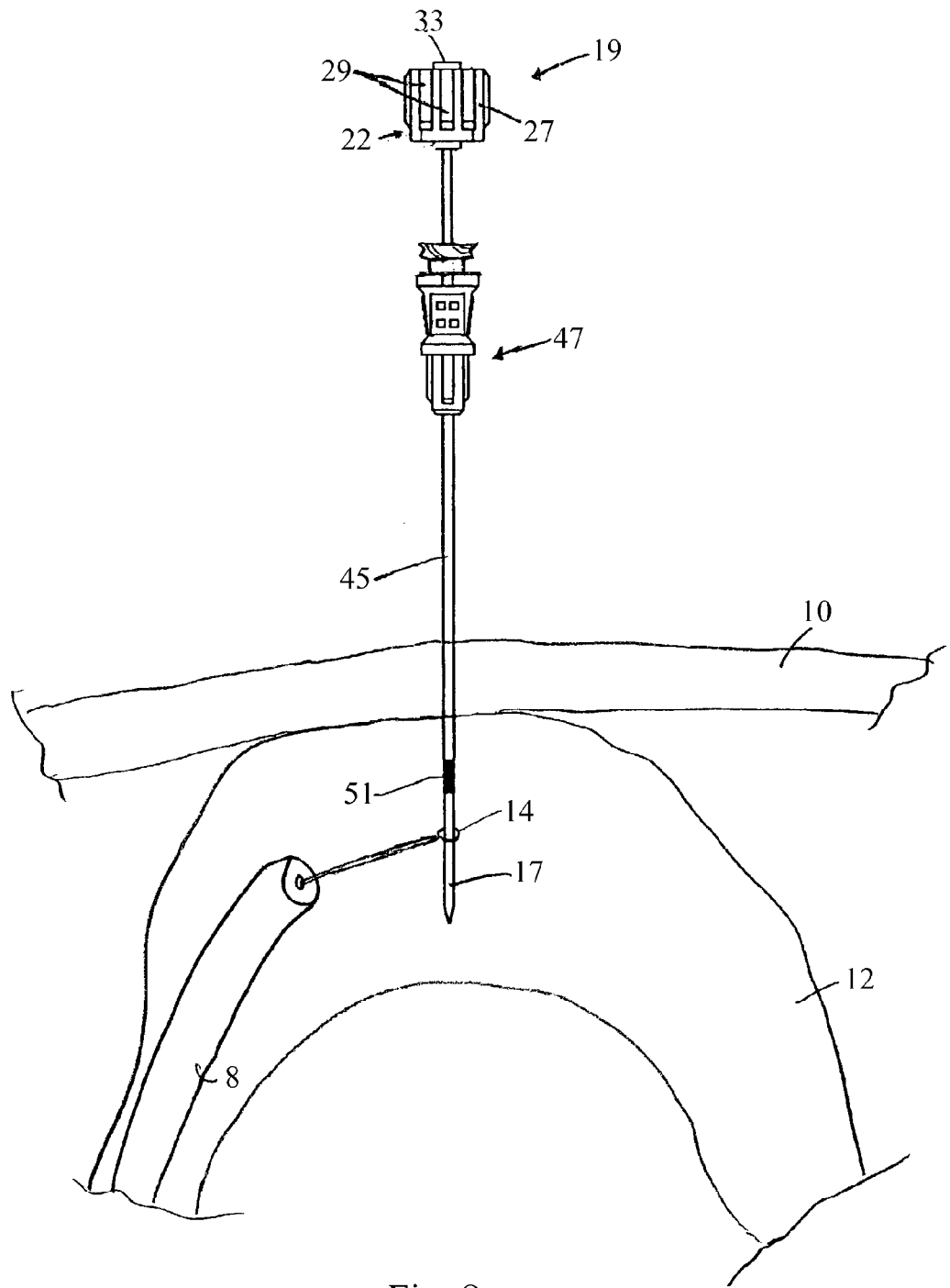
FIG. 8 is a schematic view showing the jejunum being held stationary against the abdominal wall by the combination of the access needle stylet and the endoscopic snare and also showing the access needle cannula being inserted into the jejunum.

Referring now to FIG. 8, with jejunum 12 held stationary against abdominal wall 10 by snare 14 and stylet 17, cannula 45 is de-coupled from stylet 17 (by unscrewing hub 19 from hub 47), and the distal end 53 of cannula 45 is then moved distally until it penetrates jejunum 12 through the opening previously created by stylet 17.

Figure 9:
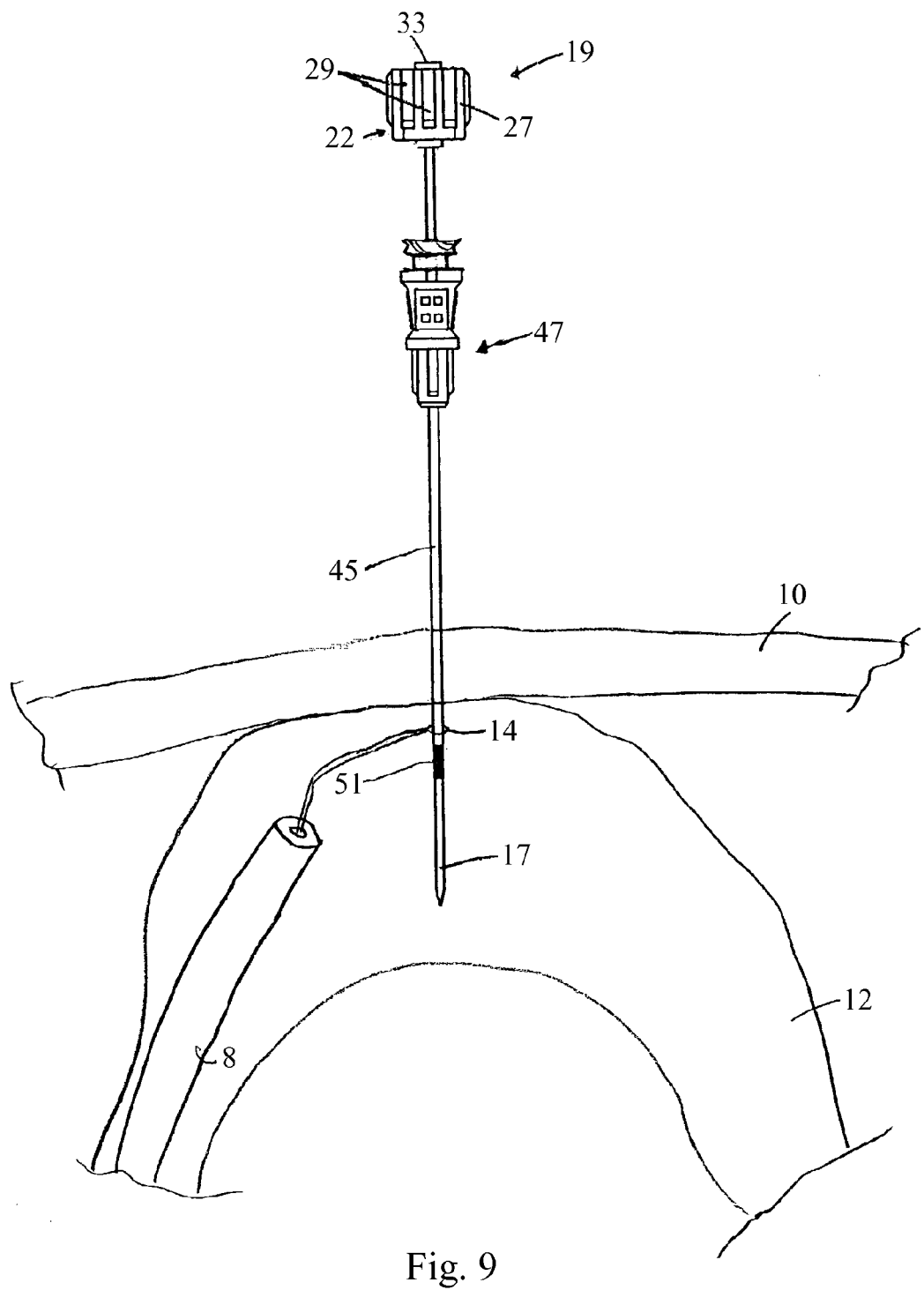
FIG. 9 is a schematic view showing the loosened snare being moved from the distal end of the stylet to the distal end of the cannula.

Referring now to FIG. 9, snare 14 is loosened slightly from the inserted portion of stylet 17 and is then moved from stylet 17 to the inserted portion of cannula 45. Snare 14 is then tightened around the inserted portion of cannula 45.

Figure 10:
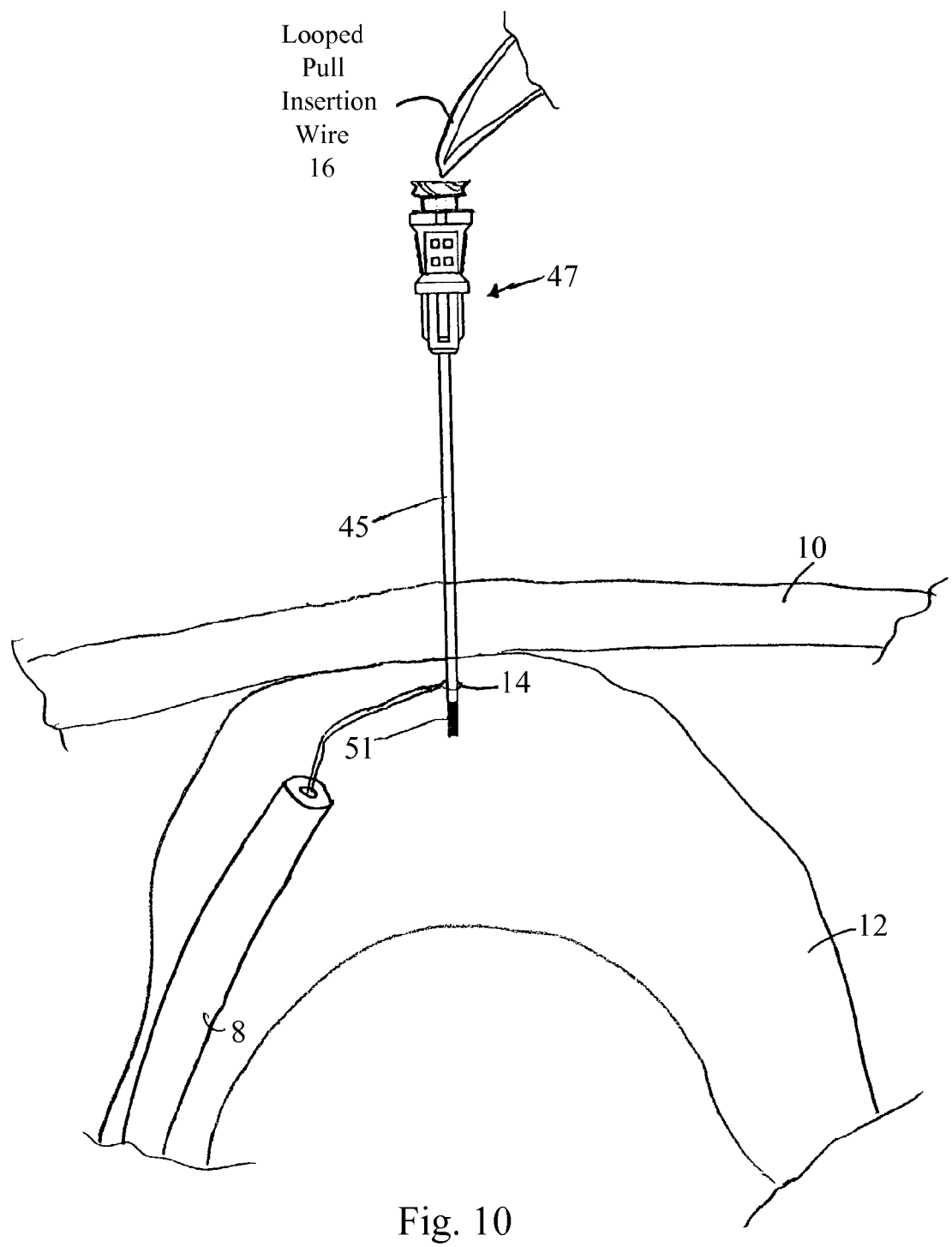
FIG. 10 is a schematic view showing the snare tightened around the cannula, the stylet withdrawn proximally from the cannula and the distal end of an insertion wire about to be inserted through the cannula and into the jejunum.

Referring now to FIG. 10, with snare 14 now tightened around cannula 45, stylet 17 is then withdrawn proximally from cannula 45. At this point, it is the combination of cannula 45 and snare 14 that hold jejunum 12 stationary against abdominal wall 10. With stylet 17 removed, the distal end of an insertion wire 16 (or a suture) is inserted through cannula 45 and into jejunum 12. Snare 14 is then moved from around the inserted portion of cannula 45 to capture the distal end of insertion wire 16. With snare 14 holding onto the distal end of insertion wire 16, snare 14 and the distal end of insertion wire 16 are then withdrawn from the patient through the jejunum, the stomach and, ultimately, the mouth of the patient.

Figure 11:
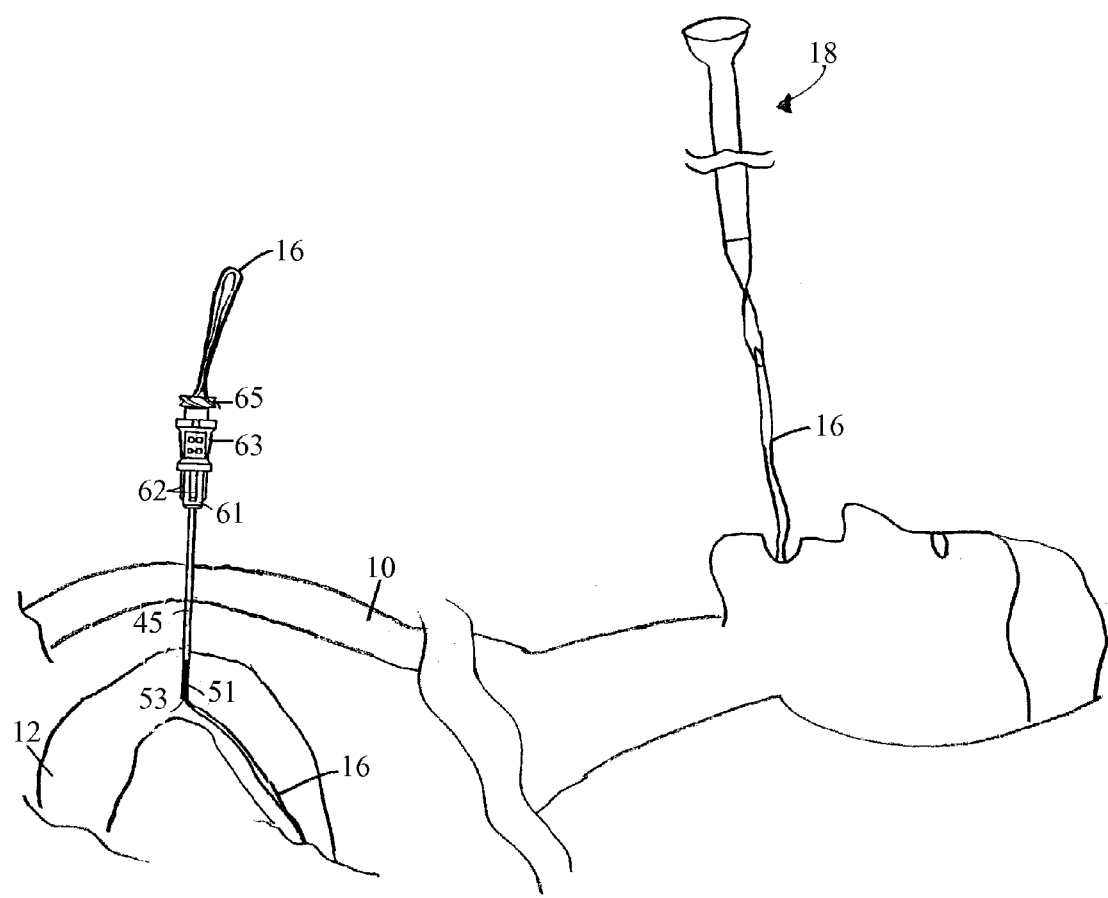
FIG. 11 is a schematic view showing a PEJ tube coupled to an insertion wire and positioned in a patient using the pull method.

Referring now to FIG. 11, a PEJ tube 18 is then attached to the distal end of insertion wire 16, which has previously been pulled out of the patient's mouth. The proximal end of insertion wire 16 is then pulled proximally, causing PEJ tube 18 to be pulled through the patient until its proximal end extends out through the abdominal wall of the patient and its distal end is disposed within the jejunum of the patient.

Figure 12:
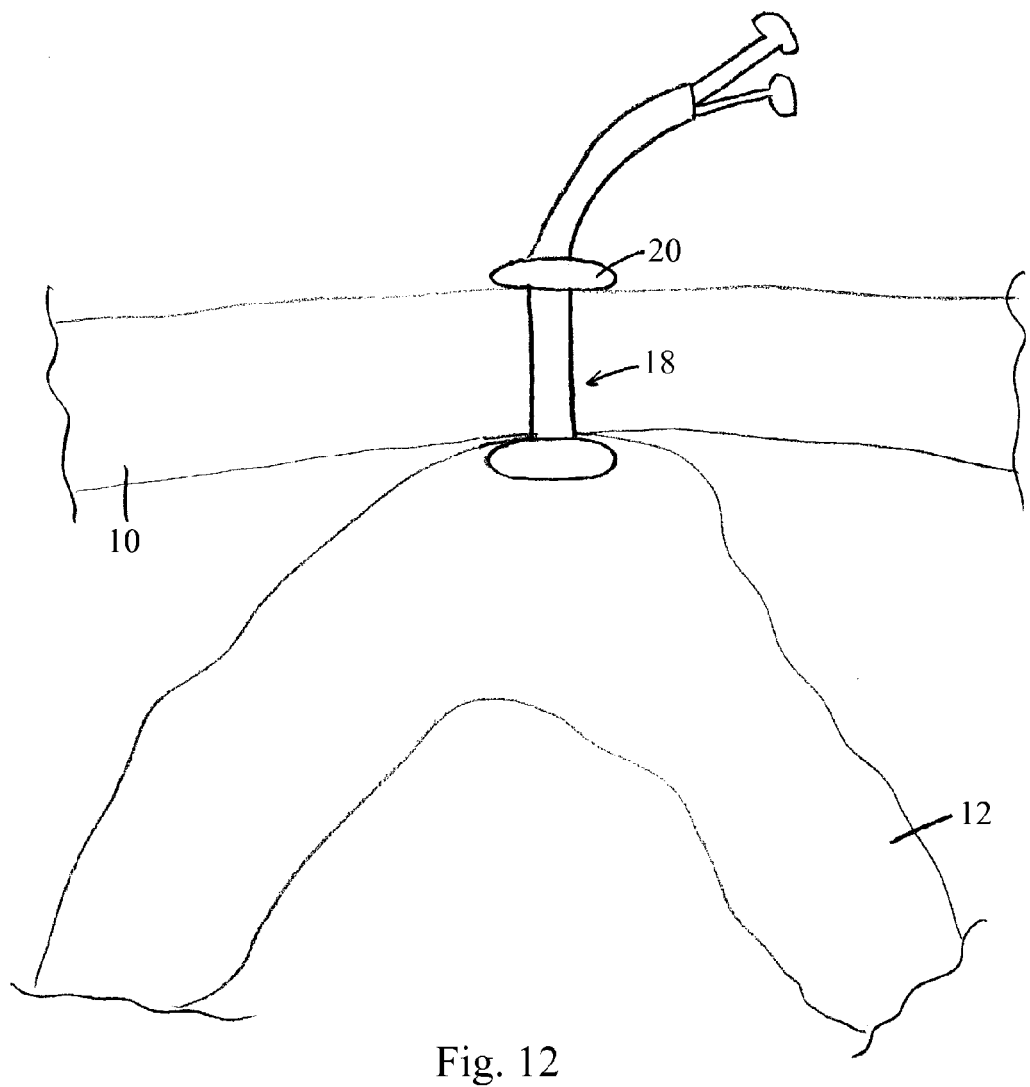
FIG. 12 is a schematic view showing a PEJ tube implanted in a patient following practice of the present method.

Referring now to FIG. 12, the distal end of PEJ tube 18 can be seen to have an enlarged end, which serves to anchor the distal end of PEJ tube 18 in jejunum 12. An external bolster 20 may be positioned over PEJ tube 18 to hold PEJ tube 18 in place on the patient. With PEJ tube 18 thus implanted, liquid nutrition materials and/or medications may be fed into the jejunum through PEJ tube 18.

It should be appreciated that, instead of positioning the PEJ tube in the patient by the pull-method as described above, the PEJ tube could alternatively be positioned in the patient using the push method.

It should also be appreciated that the foregoing method and device could also be used to implant a PEG tube in a patient or to implant other types of devices elsewhere in a patient. The present method and device could also be used, more generally, to position an organ within the body.

The embodiments of the present invention described above are intended to be merely exemplary and those skilled in the art shall be able to make numerous variations and modifications to it without departing from the spirit of the present invention. For example, although stylet 17 is described herein as being a solid member, stylet 17 could instead be hollow. In addition, although cannula 45 is disclosed herein as having a blunt distal end 53, distal end 53 could instead be tapered. Moreover, whereas hubs 19 and 47 are described herein as being secured by a twist-lock, other removable securing means, such as a latch or a clip, could be used. Also, instead of using a band to differentiate stylet 17 and cannula 45, stylet 17 and cannula 45 could be colored differently, stylet and/or cannula 45 could be provided with graduated depth markers, or stylet and/or cannula could be provided with surface markings, textures or patterns. It should also be understood that the diameters of stylet 17 and cannula 45 could be varied. In addition, barbs or like means could be provided on the distal end of stylet 17 and/or cannula 45 to facilitate the grasping thereof by the snare. Furthermore, various types of coatings (e.g., antithrombotic, antimicrobial, hydrophilic or hydrophobic) could be applied to access needle 11. All such variations and modifications are intended to be within the scope of the present invention as defined in the appended claims.

What is claimed is:

1. A method for implanting a percutaneous endoscopic jejunostomy tube in a patient, said method comprising the steps of:
  (a) providing an access needle, the access needle comprising a stylet and a cannula, the stylet being removably insertable into the cannula, wherein the distal end of the stylet extends distally for an appreciable distance beyond the distal end of the cannula;
  (b) inserting the stylet, but not the cannula, into the jejunum;
  (c) grabbing the stylet with an endoscopically-positioned snare;
  (d) anchoring the jejunum against the abdominal wall of the patient using the snared stylet;
  (e) loosening the snare slightly while advancing the cannula into the jejunum and into the loosened snare;
  (f) tightening the snare around the cannula;
  (g) removing the stylet from the cannula;
  (h) inserting a guide wire or suture through the cannula and into the jejunum; and
  (i) using the guide wire or suture to implant a PEJ tube into the patient.

2. The method as claimed in claim 1 wherein the distal end of the stylet extends distally beyond the distal end of the cannula by about 1.5 inch.

3. The method as claimed in claim 1 wherein the distal end of the cannula has a marking to facilitate distinguishing the cannula from the stylet.

4. The method as claimed in claim 1 wherein the access needle further includes a cannula hub fixed to the proximal end of the cannula and a stylet hub fixed to the proximal end of the stylet, said cannula hub being removably securable to said stylet hub to prevent unwanted longitudinal movement of said stylet relative to said cannula.

5. The method as claimed in claim 4 wherein said cannula hub and said stylet hub are threadingly engageable with one another.

6. The method as claimed in claim 4, wherein each of the cannula hub and the stylet hub is provided with gripping elements.

7. The method as claimed in claim 1, wherein the cannula has a length that is approximately two-thirds the length of the stylet.

8. The method as claimed in claim 1, wherein the stylet is solid.

9. The method as claimed in claim 1, wherein the PEJ tube is a pull-type PEJ tube.

10. A method for implanting a tube in a patient, the method comprising the steps of:
 (a) providing an access needle, the access needle comprising a stylet and a cannula, the stylet being removably insertable into the cannula, wherein the distal end of the stylet extends distally beyond the distal end of the cannula;
 (b) inserting the distal end of the stylet, but not the cannula, through the abdominal wall of the patient and into a body organ;
 (c) grabbing the distal end of the stylet with a snare;
 (d) anchoring the body organ against the abdominal wall of the patient using the snared stylet;
 (e) loosening the snare while advancing the distal end of the cannula into the body organ and into the loosened snare;
 (f) tightening the snare around the distal end of the cannula;
 (g) removing the stylet from the cannula;
 (h) inserting a guide wire or suture through the cannula and into the body organ; and
 (i) using the guide wire or suture to implant a tube into the patient.

11. The method as claimed in claim 10, wherein the distal end of the stylet extends distally beyond the distal end of the cannula by about 1.5 inch.

12. The method as claimed in claim 10, wherein the distal end of the cannula has a marking to facilitate distinguishing the cannula from the stylet.

13. The method as claimed in claim 10, wherein the access needle further includes a cannula hub fixed to the proximal end of the cannula and a stylet hub fixed to the proximal end of the stylet, said cannula hub being removably securable to said stylet hub to prevent unwanted longitudinal movement of said stylet relative to said cannula.

14. The method as claimed in claim 13, wherein said cannula hub and said stylet hub are threadingly engageable with one another.

15. The method as claimed in claim 13, wherein each of the cannula hub and the styled hub is provided with gripping elements.

16. The method as claimed in claim 10, wherein the cannula has a length that is approximately two-thirds the length of the stylet.

17. The method as claimed in claim 10, wherein the stylet is solid.

\* \* \* \* \*